United States Patent [19]

Kirsch

[11] Plant 5,200

[45] Mar. 6, 1984

[54] LILY NAMED WHITE DREAM

[75] Inventor: Ted T. Kirsch, Myrtle Point, Oreg.

[73] Assignee: Sun Valley Bulb Farms, Inc., Myrtle Point, Oreg.

[21] Appl. No.: 422,203

[22] Filed: Sep. 23, 1982

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Chas W. Rummler

[57] ABSTRACT

A new and distinct variety of Oriental Hybrid lily plant of the Parkmanni type, particularly distinguished by its large 6 to 8 white, slightly down-facing, bow-shaped flowers which are borne in a raceme arrangement on long strong stems and outwardly-projecting pedicels, usually with one bud or flower on each pedicel, and by its dark glossy green and relatively disease-resistant foliage.

2 Drawing Figures

BACKGROUND OF THE NEW PLANT

This new variety of lily plant originated as a seedling of unkown parentage growing among similar plants at my nursery in Arcata, Calif. The large, white, slightly down-facing flowers and the dark green, relatively disease-free foliage prompted me to select this plant for propagation, which I did asexually, with the result that I found this plant to have advantageous and distinctive characteristics which make it a valuable addition to the field of commercial lily cut flower culture. Propagation of this new lily at Arcata, Calif., through successive generations by means of scales and tissue culture has revealed that the distinctive characteristics of this plant hold true from generation to generation and appear to be firmly fixed.

DESCRIPTION OF THE DRAWING

This new variety of lily plant is illustrated by the accompanying full-color photographic drawing which shows a full-grown blooming plant in the left view and a close-up of several blooms in the right view, the color rendition being as nearly true as can be obtained by conventional photographic procedures.

DESCRIPTION OF THE NEW PLANT

The following is a detailed description of my new variety of lily plant based on observations of greenhouse-grown plants at Arcata, Calif., in the spring of 1982, with color designations according to the R.H.S. Colour Chart published by The Royal Horticultural Society of London, England.

THE PLANT

Orgin: Seedling.
Parentage: Unknown.
Classification: Oriental Hybrid, Parkmanni type.
Form: Tall single stem from each bulb.
Height: 2½ to 4 feet at maturity.
Growth: Sturdy and upright with excellent strength.
Cane size: Stems grown from ¼ inch in diameter from small bulbs to ½ inch in diameter from larger bulbs.
Foliage:
*Leaves at the flower cluster.*—Two in number, one at the base of each pedicel, 4½ to 5 inches long and 1 to 1¾ inches wide, and the other on the pedicel 1½ to 2½ inches from the flower, 4 to 4½ inches long and ¾ to 1 inch wide.
Shape of leaf: Lanceolate (almost elliptical).
*Texture.*—Leathery.
*Aspect.*—Smooth.
*Ribs and veins.*—Distinct parallel veins from base to tip.
Bublets (Underground): Occurrence: One to three on each healthy, normal plant at digging time.
*Size.*—From ¼ inch to 1 inch in diameter.
*Color.*—White, with occasional pink shading at the tips.
Bulbs:
*Size.*—From ½ inch to 12 inches in circumference, depending on age.
*Color.*—White, with yellow and pink overtones. As bulbs becomes larger and older, the overtones of yellow and pink become more prominent.

THE BUD

Form: Elliptical with acute apex.
Size: Averaging about 3½ to 4 inches long and 1 to 1½ inches wide.
Number: Usually one on each pedicel, with 1 to 10 buds on a plant according to culture and bulb size.
Opening rate: Normal; buds open successively from the lowermost bud to the top bud which is the last to open.
Color: White; the midrib has pink overtones as does the base of the bud.
Surface: Rugose, leathery, with prominent veins.
Pedicel: Strong, long and generally outfacing.
*Color.*—Green underneath; green with maroon splotches on top. Angled about 60° from vertical. Glabrous, glaucous.
*Length.*—4 to 7 inches.

THE FLOWER

Blooming habit: Annually, blooming profusely in July when forced in the greenhouse under normal temperature and cultural conditions.
Size: Large, averaging 6 to 8 inches in diameter.
Borne:
*From larger bulbs.*—The inflorescence has a raceme arrangement with each pedicel bearing one bud. The size of the bulb and its culture care will determine the number of blooms and buds to be found on any given inflorescence. From large bulbs, this lily may have 3 to 6 blooms open at one time.

Shape: Bow-shaped, with uniformaly-spaced petals in a star arrangement with the tips of the petals recurving slightly.

Petalage: Normal, three sepals and three petals.

*Form.*—Oval with obtuse apex and a center furrow bisecting each petal longitudinally. The edges slightly undulate.

*Size.*—The petals are about 4 to 5 inches long and 2 to $2\frac{1}{2}$ inches wide.

*Color.*—Upper side: Upon opening, the whole petal is R.H.S. White 155-D. The midrib is light green at the base, turning white about 1 inch from the base. The middle half of the petal is covered with numerous spots R.H.S. Red 54-A. Under side: R.H.S. White 155-D. The midrib is light purple at the base, turning lighter and more green towards the tip.

*Papillae.*—10 to 20 present on the base of the petal.

*Texture.*—Leathery.

*Aspect.*—Velvety.

Fragrance: Sweet.

Discoloration: Stays the same color, but petals become more transparent (less opaque).

Effect of weather: The flowers are generally not affected by wet weather, but flowers age faster as temperature rises.

Persistance: The flowers tend to hang on and dry.

Lasting quality:

*On the plant.*—Two to three weeks depending on the size of the bulb and its environmental temperature.

*As a cut flower.*—10 to 14 days.

REPRODUCTIVE ORGANS

Stamens: Six in number, evenly-spaced around pistil.

*Anthers.*—R.H.S. Greyed Orange 169-C, about $\frac{3}{4}$ inch long.p2 *Filaments.*—White at base, turning greener towards tip, about 3 inches long.

Pistils: One in number.

*Style.*—Green, 3 inches long.

*Stigma.*—Purple.

*Ovary.*—Classified as a schizocarp, $1\frac{1}{2}$ inches long and 1 inch in diameter, dehiscing into thirds and containing six rows of seeds of the usual shape for lilies.

I claim:

1. A new and distinct variety of Oriental Hybrid lily plant substantially as herein shown and described, characterized by its large, white, slightly down-facing flowers borne on long, strong, outwardly projecting pedicels having petals that are moderately covered with red spots and recurve slightly at their tips, by its dark green and relatively disease-free foliage, and by blooms that are relatively long lasting whether on the plant or as cut flowers.

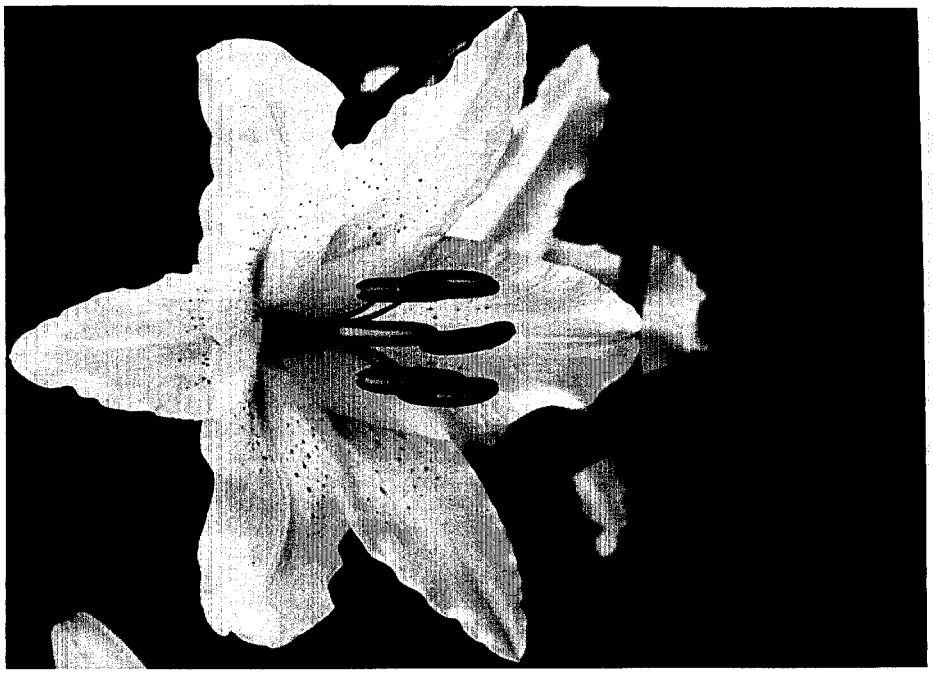
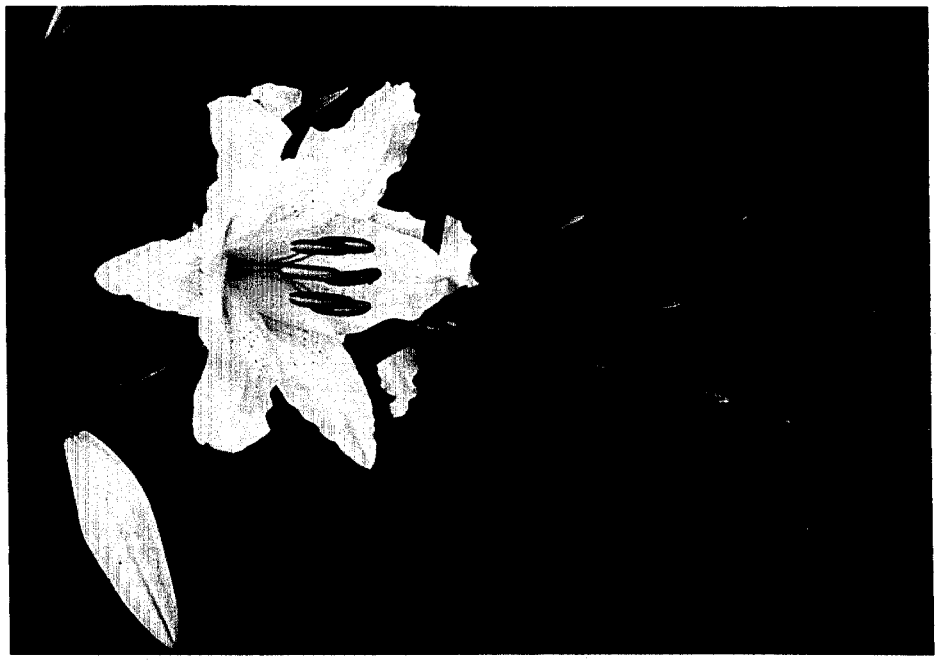

* * * * *